United States Patent
Dong et al.

(10) Patent No.: US 12,247,953 B2
(45) Date of Patent: Mar. 11, 2025

(54) DEVICE FOR CREEP TEST, SYSTEM FOR TENSILE AND COMPRESSIVE CREEP TEST AND TEST METHOD OF THE SAME

(71) Applicant: Southwest Forestry University, Kunming (CN)

(72) Inventors: Chunlei Dong, Kunming (CN); Jie Wang, Kunming (CN); Hui Wan, Kunming (CN)

(73) Assignee: Southwest Forestry University, Kunming (CN)

( * ) Notice: Subject to any disclaimer, the term of this patent is extended or adjusted under 35 U.S.C. 154(b) by 343 days.

(21) Appl. No.: 17/867,756

(22) Filed: Jul. 19, 2022

(65) Prior Publication Data

US 2024/0027315 A1   Jan. 25, 2024

(51) Int. Cl.
*G01N 3/08* (2006.01)
*G01N 33/46* (2006.01)

(52) U.S. Cl.
CPC ............... *G01N 3/08* (2013.01); *G01N 33/46* (2013.01); *G01N 2203/0017* (2013.01); *G01N 2203/0019* (2013.01); *G01N 2203/0071* (2013.01); *G01N 2203/0222* (2013.01)

(58) Field of Classification Search
CPC .. G01N 3/08; G01N 33/46; G01N 2203/0017; G01N 2203/0019; G01N 2203/0071; G01N 2203/0222; G01N 2203/0033; G01N 3/04; G01N 3/14; G01N 2203/0682
See application file for complete search history.

(56) References Cited

U.S. PATENT DOCUMENTS

| | | | | |
|---|---|---|---|---|
| 4,031,746 A * | 6/1977 | Furuta | .................... | G01N 3/068 73/834 |
| 4,535,636 A * | 8/1985 | Blackburn | ............... | G01N 3/14 73/831 |
| 2004/0107776 A1* | 6/2004 | Honer | ...................... | G01N 3/00 73/746 |

FOREIGN PATENT DOCUMENTS

CN          111442993 A         3/2020

* cited by examiner

*Primary Examiner* — Xin Y Zhong
(74) *Attorney, Agent, or Firm* — Paschall & Associates, LLC; Mark Goldberg

(57) ABSTRACT

A device for a creep test and a test system and a method using the device are provided. The device for the creep test includes a device frame, a test piece clamp, a load loading mechanism and linear displacement sensors. A test piece is arranged in a middle of the test piece clamp. A first end of the test piece clamp is a fixed end, a position of the fixed end is unchanged relative to the device frame. A second end of the test piece clamp is a movable end. The load loading mechanism includes a pulley block and a load. A system for a tensile and compressive creep test includes a box body which is sealable. The box body is provided with a box door which is provided with a constant temperature and humidity device. The device for the creep test is arranged in the box body.

19 Claims, 15 Drawing Sheets

DEVICE FOR CREEP TEST, SYSTEM FOR TENSILE AND COMPRESSIVE CREEP TEST AND TEST METHOD OF THE SAME

TECHNICAL FIELD

The present disclosure relates to a device for testing physical and mechanical properties of bamboo/wood-based materials and relates to a system for a tensile and compressive creep test.

BACKGROUND ART

Wood, bamboo or bamboo-based materials are renewable green and environment-friendly building materials. However, although the creep performance, one of the important indexes for measuring the long-term service performance of the wood, bamboo or bamboo-based materials, has been researched for more than half a century, a large controversy exists on the mechanism of occurrence and development and quantitative prediction of the creep performance in academic and engineering communities. In particular, Normal Creep and Mechanical Sorptive Creep (MSC) of such materials in natural service environments (namely, temperature-variable and humidity-variable environments) has been a hot and difficult problem of academic research, and a test system capable of simultaneously simulating natural service environments and automatically measuring, presenting and preserving creep deformation is the key to researching and solving such problems.

In the prior art, static bending creep is mostly used for researching creep of wood or bamboo. For example, a Chinese invention patent application of "DEVICE FOR CREEP TEST, SYSTEM FOR WOOD CREEP TEST AND TEST METHOD USING THE SAME" (with the application number of 2020102392173) filed by the applicant on Mar. 30, 2020 disclosed a device for a creep test and a test system comprising an improved device for a creep test. The system for the wood creep test provided by the present disclosure can be configured for testing a certain number of test piece samples while carrying out a creep test on wood. The whole system of the present disclosure can continuously and stably detect, record and display common creep and complex wet creep deflection, dry shrinkage and wet expansion amount and environmental temperature and humidity parameters of wood for a long time, and a test basis and a test platform are provided for exploration of wood MSC behavior rules and creep mechanisms.

The wood/bamboo is researched by using single static bending creep, resulting in the unavoidable problem that the static bending creep of the material is actually the coupling of the compressive creep of the upper half part of the material and the tensile creep of the lower half part of the material from the perspective of stress analysis. Due to the anisotropic special wood properties of wood and bamboo, the mechanical properties of the wood and bamboo in tensile, compressive and static bending stress states are different. For example, the tensile elastic modulus of most wood is 1.1-1.2 times of the bending elastic modulus and is about 1.1 times of the compressive elastic modulus. More importantly, the basic physical and mechanical properties of the wood in the stress direction are inconsistent due to the influence of the temperature-variable and humidity-variable environment. Therefore, researching the creep performance of the wood/bamboo by using the single static bending creep will cover the special creep rule and performance of the wood/bamboo in the pure pulling and pure pressing stress states, and the research method also has great problems from the perspective of scientific research due to the doping of the tensile and compressive dry shrinkage and wet expansion of the wood/bamboo and the huge difference of the sensitivity of the wood/bamboo to the environment temperature and humidity.

Research on the creep performance of the bamboo-wood based material in the current tensile/compressive mode is at the primary stage. Due to the limitation of the environmental temperature and humidity control system and a space thereof, most of the current research is concentrated in a pure test piece creep test under indoor or outdoor conditions, and the research on tensile/compressive creep in the state that the environmental temperature and humidity may be greatly regulated and controlled is lacking. If a creep test is carried out by utilizing an existing tensile/compressive instrument, the equipment is expensive, the test method is single, and the test content and the test data are tedious and old. Therefore, in the prior art, a device for a creep test in a tensile/compressive mode capable of automatically acquiring, processing, storing and visually presenting test creep data is lacking, which greatly restricts deep development of related research.

SUMMARY

In order to overcome the defects in the prior art, the present disclosure provides a device for a creep test and a test system using the device. Long-term automatic acquisition, storage and display of pure tensile and pure compressive creep of bamboo/wood-based materials in a high-precision controllable climate environment can be realized. The creep test precision reaches 0.001 mm. The precision requirement of wood/bamboo creep tests is completely met. Moreover, through simple transformation of a test piece clamp and a pulley block, free switching of tensile creep and compressive creep can be realized on one set of system, and large miniaturization and light weight of equipment are realized.

The present disclosure is realized through the following technical solution.

The device for the creep test at least includes a device frame, a test piece clamp, a load loading mechanism and linear displacement sensors. Each of the test piece clamp, the load loading mechanism and the linear displacement sensors is arranged on the device frame. The test piece clamp is configured for placing a test piece for the creep test. The test piece is arranged in a middle of the test piece clamp. A first end of the test piece clamp is a fixed end. A position of the fixed end is unchanged relative to the device frame. A second end of the test piece clamp is a movable end. The load loading mechanism includes a pulley block and a load. The pulley block includes at least one movable pulley and multiple fixed pulleys. The load is connected with the movable end of the test piece clamp through a steel wire rope that is wound around the pulley block. An acting force is applied to the test piece for the creep test by the load through the movable end of the test piece clamp. The acting force acts on a same line as a central axis of the test piece. The linear displacement sensors are configured for acquiring displacement data of the test piece during the creep test.

The device frame may include a top plate and a bottom plate which may be arranged up and down opposite to each other. The top plate and the bottom plate may be fixedly connected through at least four supporting rods which may be arranged parallel to each other.

A direction of the acting force applied to the test piece clamp may be parallel to extending directions of the at least four supporting rods. The load loading mechanism may be arranged above the test piece clamp. The multiple fixed pulleys of the load loading mechanism may be fixed on the top plate.

The fixed end and the movable end of the test piece clamp may be fixedly provided with respective clamp seat plates. Four supporting rods of the at least four supporting rods may vertically penetrate through the clamp seat plates. A position of one of the clamp seat plates which may be located at the fixed end may be unchanged relative to the four supporting rods. Another one of the clamp seat plates which may be located at the movable end may be slideable along the extending directions of the four supporting rods, so that a tensile or compressive acting force is applied to the test piece on the test piece clamp.

According to a device for a tensile and creep test of the present disclosure, the one of the clamp seat plates on the test piece clamp may be close to the bottom plate and may be fixedly connected with the bottom plate to serve as the fixed end. The another one of the clamp seat plates may be away from the bottom plate to serve as the movable end, and may be connected with the steel wire rope of the load loading mechanism. The load generates the acting force on the movable end after the steel wire rope is wound around the pulley block. The clamp seat plate is located at the movable end on the side which is close to the top plate relative to the test piece, so that a tensile acting force is generated on the test piece.

According to a device for a compressive and creep test of the present disclosure, the one of the clamp seat plates on the test piece clamp may be away from the bottom plate and may be fixedly connected with the bottom plate to serve as the fixed end. The another one of the clamp seat plates may be close to the bottom plate to serve as the movable end, and may be connected with the steel wire rope of the load loading mechanism. The load generates the acting force on the movable end after the steel wire rope is wound around the pulley block. Since the clamp seat plate located at the movable end is on the side which is close to the bottom plate relative to the test piece, so that the compressive acting force is generated on the test piece.

In some embodiments, a load seat plate parallel to the clamp seat plates may be arranged at a tail end of the steel wire rope. The four supporting rods may vertically penetrate through the load seat plate which may be in sliding fit with the four supporting rods. The load seat plate may be fixedly connected with the another one of the clamp seat plates which may be at the movable end of the test piece clamp. The acting force of the pulley block may be uniformly applied to the movable end of the test piece clamp through the load seat plate, so that the stability and the effectiveness of the acting force are guaranteed.

The at least one movable pulley may be arranged above the load seat plate and rotatably connected with the load seat plate. That is, the load seat plate is equivalent to a part of the movable pulley to move along with the movable pulley.

The multiple fixed pulleys may include two fixed pulleys. A first fixed pulley of the two fixed pulleys may be arranged above the at least one movable pulley. A second fixed pulley of the two fixed pulleys may be arranged on one side of the first fixed pulley. The first fixed pulley and the second fixed pulley may be rotatably connected with the top plate, an axle of the first fixed pulley, an axle of the second fixed pulley and an axle of the movable pulley are parallel to each other. The first fixed pulley and the movable pulley are arranged up and down, which may guarantee that the acting force transmitted from the load through the steel wire rope may vertically act on the load seat plate.

The at least one movable pulley and the first fixed pulley may be each be a three-wheel pulley set, the second fixed pulley is a single wheel pulley. The steel wire rope may be wound between the movable pulley and the first fixed pulley and finally is wound the second fixed pulley. The steel wire rope is wound between the movable pulley and the first fixed pulley in two ways, that is, the tail end of the steel wire rope is either connected to a hook of the movable pulley or a hook of the first fixed pulley, so that two acting force amplification ratios of the load being 1:7 or 1:6 may be generated.

In some embodiments, the tail end of the steel wire rope may be connected with a hook of the at least one movable pulley. The steel wire rope may be wound between the movable pulley and the first fixed pulley for three circles, led out from the movable pulley and wound around the second fixed pulley. A front end of the steel wire rope may be connected vertically downwards to the load. Therefore, an acting force amplification effect of 1:7 may be generated.

The linear displacement sensors may include two linear displacement sensors. Each of the two linear displacement sensors may be fixedly connected with a nearest supporting rod of the at least four supporting rods through respective sensor support. Directions of probes of the two linear displacement sensors may be opposite. Two bearing platforms may be arranged in a middle of the test piece in the test piece clamp. For each of the two bearing platforms, a first end of the bearing platform may be fixedly connected with the test piece, and a second end of the bearing platform may extend to a front of a corresponding one of the probes of the two linear displacement sensors. The bearing platforms are fixed at two ends of an effective section of the test piece, and test values obtained by the linear displacement sensors are variable quantities of the effective section of the test piece.

According to the device for the tensile and creep test of the present disclosure, further, the test piece clamp may include two tensile clamp seats. Each of the two tensile clamp seats may be fixed on a corresponding one of the clamp seat plates. Open grooves may be respectively formed in the two tensile clamp seats. Each of the open grooves may have two opposite sides and an opening between ends of the two sides. The open grooves of the two tensile clamp seats may be opposite to each other. Two ends of the test piece may be respectively limited in the open grooves of the two tensile clamp seats.

Inner walls of the two sides of each of the open grooves may be provided with anti-slip patterns. Each of the open grooves may be a dovetail groove. The anti-skid lines can effectively prevent the test piece from displacing in the open grooves due to the acting force.

In order to preferably prevent the test piece from moving along the direction of the acting force in the open grooves due to the acting force, each open groove may be a dovetail groove.

The inner walls of the open groove may be smooth. One wedge-shaped sliding block may be arranged between the test piece and one of the inner walls of the two sides of the open groove. Another one of the wedge-shaped sliding blocks may be arranged between the test piece and another one of the inner walls of the two sides of the open groove. A shape of a side-view projection of each of the one wedge-shaped sliding block and the another one wedge-shaped sliding block may be a right trapezoid shape. A face, which may be attached to the test piece, of each of the one wedge-shaped sliding block and the another one wedge-shaped sliding block may be a vertical face. Anti-slip patterns may be arranged on the vertical face. The vertical faces of the wedge-shaped sliding blocks contact with the test piece and clamp the test piece. The two ends of the test piece do not need to be machined into the same cross section shape (trapezoid) as the open groove and may be directly machined into a pair of parallel planes, so that machining difficulty of the test piece is reduced. The anti-skid patterns on the vertical face can prevent the test piece from displacing in the acting force direction relative to the wedge-shaped sliding block.

Puller bolts may be arranged on a bottom portion, which may be opposite to the opening of a corresponding one of the open grooves, of each of the two tensile clamp seats. Each of the puller bolts and a corresponding one of the one wedge-shaped sliding block and the another one wedge-shaped sliding block may be arranged in one-to-one correspondence. Each of the puller bolts may penetrate through the bottom portion of a corresponding one of the two tensile clamp seats and may abut against an end, which may be close to the bottom portion, of a respective one of the one wedge-shaped sliding block and the another one wedge-shaped sliding block. Each of the puller bolts may be in screw-thread fit with the corresponding one of the two tensile clamp seats. The wedge-shaped sliding blocks are pushed towards an opening direction of the open groove through the puller bolts, and transverse pressure on the two sides of the end of the test piece may be generated, so that a better limiting effect of the test piece is achieved.

A limiting rod may be arranged adjacent to the opening of each of the open grooves. Two ends of the limiting rod may be fixedly connected with a corresponding one of the two tensile clamp seats. The limiting rod can not only strengthen a clamping force of the wedge-shaped sliding blocks on the two sides of the end of the test piece, but also prevent the wedge-shaped sliding blocks from sliding in the open groove.

According to the device for the compressive and creep test of the present disclosure, in some embodiments, the test piece clamp may include two pressure plates. Each of the two pressure plates may be fixed on a corresponding one of the clamp seat plates. The two pressure plates may be provided with respective limiting grooves. The limiting grooves of the two pressure plates may be opposite to each other. Each of the two ends of the test piece may be limited in a corresponding one of the limiting grooves of the two pressure plates. The limiting groove can prevent the test piece from displacing in a direction of a non-acting force.

The tensile and compressive creep test system provided by the present disclosure includes a box body which is sealable. The box body is provided with a box door, the box body is provided with a constant temperature and humidity device, and wherein at least one device for the creep test is arranged in the box body.

A rack configured for fixing the at least one device for the creep test may be arranged in the box body. The at least one device for the creep test may be arranged on the rack. A top of the device frame of each of the at least one device for the creep test may be horizontally fixed to a top of the rack. A length of the top plate and a length of the bottom plate of the device frame may be equal to a width of the top of the rack.

A length of each of the clamp seat plates may be equal to a length of the load seat plate. The length of each of the clamp seat plates and the length of the load seat plate may be smaller than the length of the bottom plate. The supporting rods may include six supporting rods. Two of the six supporting rods which may be close to the box door may be connected with the top plate and the bottom plate. The other four of the six supporting rods may be connected with the top plate and the bottom plate and may penetrate through the clamp seat plates and the load seat plate.

The load of the load loading mechanism of each of the at least one device for the creep test may be arranged close to the box door.

The first fixed pulley and the second fixed pulley of the load loading mechanism may be arranged side by side along a center line of the top plate in a length direction of the top plate. The at least one movable pulley may be located directly under the first fixed pulley. A central axis and a gravity center of the first fixed pulley, a central axis and a gravity center of the at least one movable pulley, a central axis and a gravity center of the load seat plate, a central axis and a gravity center of each of the clamp seat plates, a central axis and a gravity center of the test piece clamp and a central axis and a gravity center of the test piece may be on a same vertical line, so that it can be guaranteed that the acting force can be effectively transmitted to the test piece.

A lifting device may be arranged directly under the load and placed on the bottom plate. The lifting device may be a jack.

A buffer cushion may be laid on the bottom plate that is directly under the load. The buffer cushion is mainly configured for preventing equipment damage caused by falling of the load when the test piece is pulled and broken by the load in a test process.

A test method of a system for a tensile and compressive creep test in the present disclosure includes: for each of at least one device for the creep test comprised in the system for the tensile and compressive creep test, selecting a test piece clamp according to a test purpose, installing a test piece to be tested in the test piece clamp, fixing one clamp seat plate that is provided at a fixed end of the test piece clamp, and connecting fixedly another one clamp seat plate that is provided at a movable end of the test piece clamp with a load seat plate; installing bearing platforms on the test piece, fixing positions of the linear displacement sensors, and abutting a probe of each of the linear displacement sensors against a surface of a corresponding one of the bearing platforms; placing a lifting device on a bottom plate, and lifting a load by the lifting device and connecting the load with a steel wire rope; lowering the lifting device until the load is suspended, taking out the lifting device, and laying a buffer cushion on the bottom plate that is directly under the load; closing a box door, starting a constant temperature and humidity device to control temperature and humidity in the box body, and monitoring data in real time; and inputting the temperature, the humidity and an air speed and displacement signals of the test piece in the box body into a computer for data storage, processing analysis and display.

DETAILED DESCRIPTION OF THE EMBODIMENTS

Figure 1:
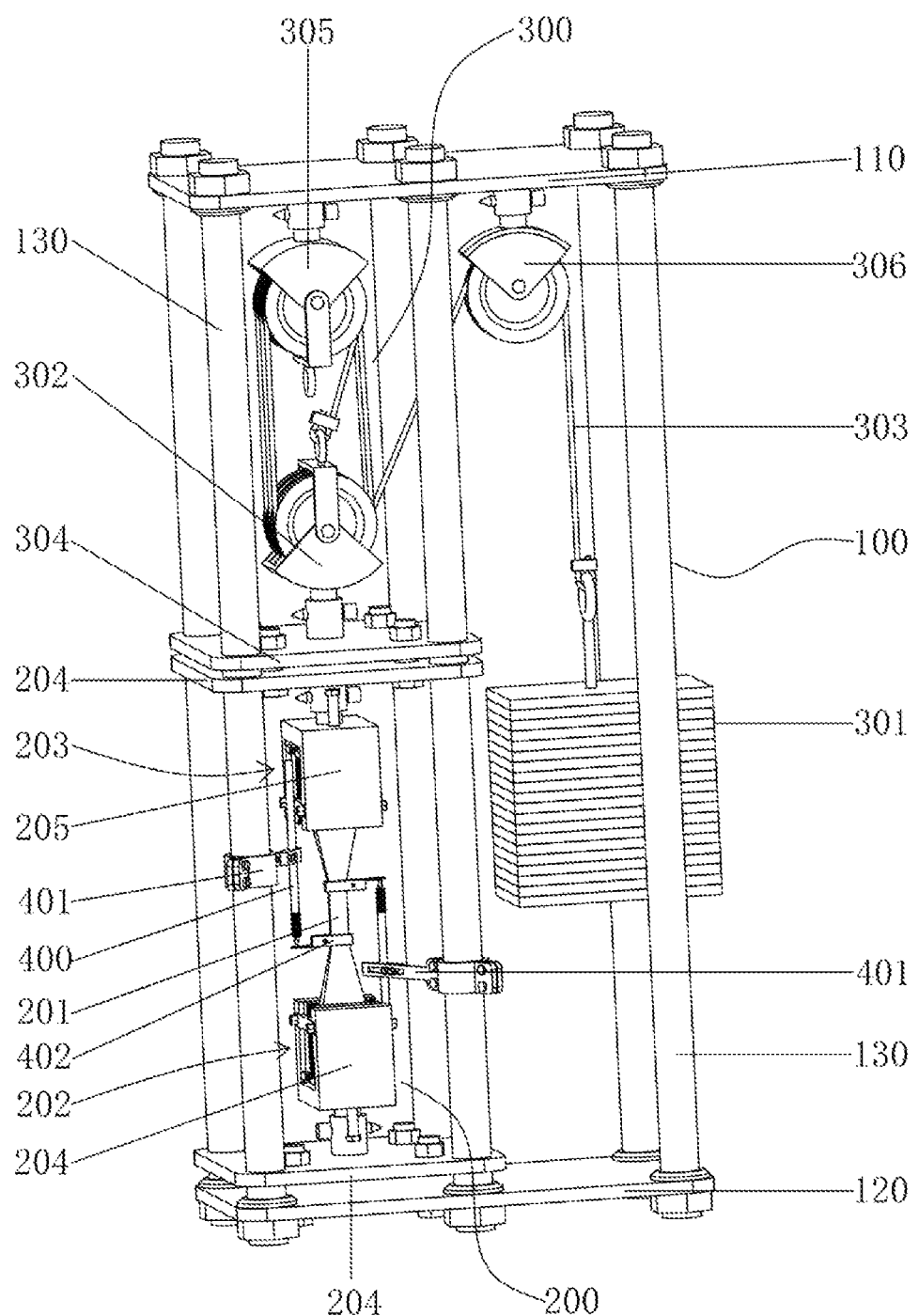
FIG. 1 is a three-dimensional schematic diagram of a device for a tensile and creep test according to the present disclosure.

As shown in FIG. 1 to FIG. 5, a device for a creep test of the present disclosure includes a device frame 100, a test piece clamp 200, a load loading mechanism 300 and linear displacement sensors 400. The test piece clamp 200, the load loading mechanism 300 and the linear displacement sensors 400 are all arranged on the device frame 100.

In the embodiment, the device frame 100 includes a top plate 110 and a bottom plate 120 which are arranged up and down opposite to each other. The top plate 110 and the bottom plate 120 are fixedly connected through at least four supporting rods 130 which are arranged parallel to each other.

The test piece clamp 200 is configured for placing a test piece 201 for the creep test. The test piece 201 is arranged in a middle of the test piece clamp 200. One end of the test piece clamp 200 is a fixed end 202, a position of the fixed end 202 is unchanged relative to the device frame 100, and an other end of the test piece clamp 200 is a movable end 203.

Figure 3:
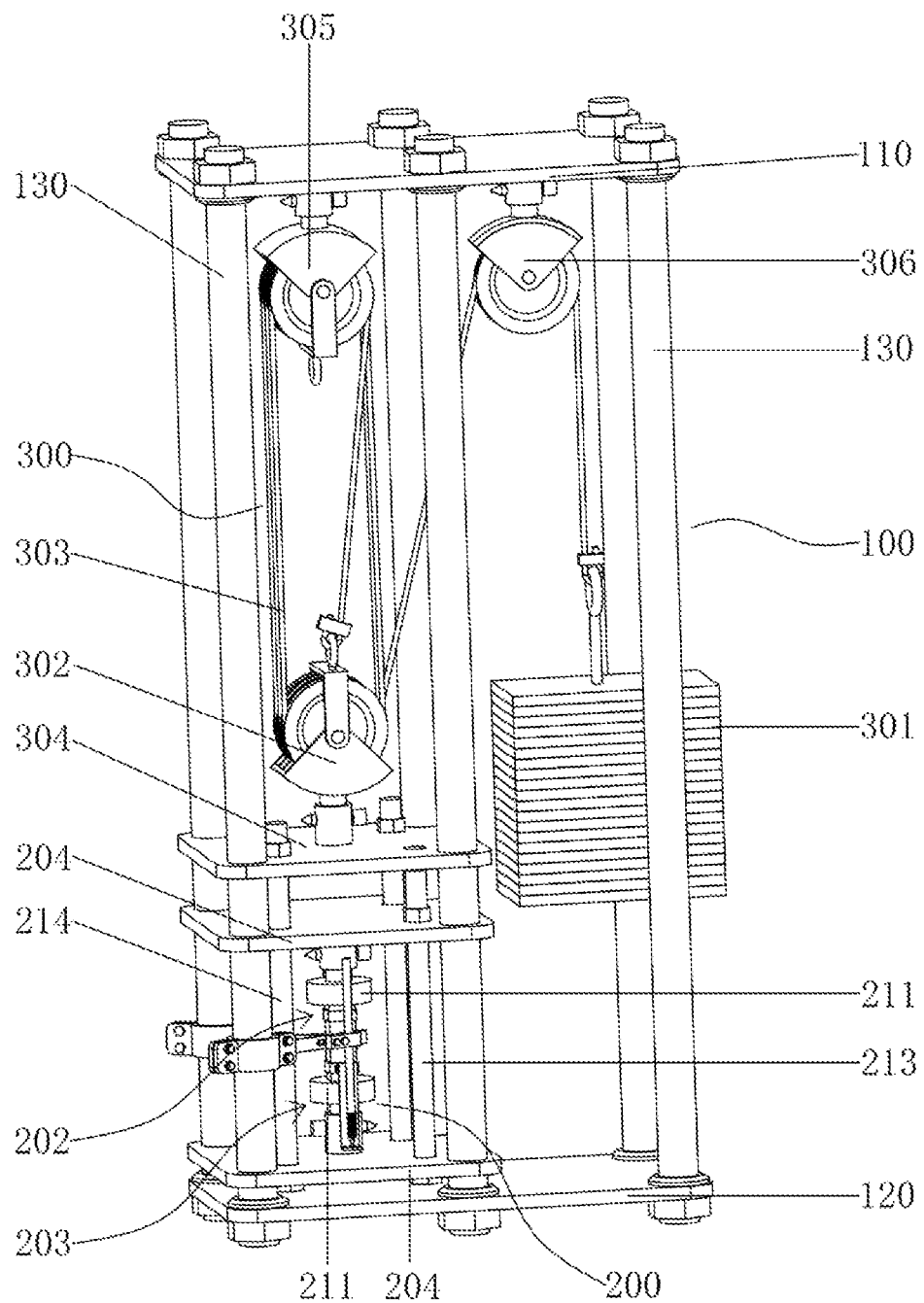
FIG. 3 is a three-dimensional schematic diagram of a device for a compressive and creep test according to the present disclosure.

In order to facilitate the test piece clamp 200 to be connected with the device frame 100, the fixed end and the movable end of the test piece clamp 200 are fixedly provided with respective clamp seat plates 204 respectively. Four supporting rods 130 vertically penetrate through the clamp seat plates 204. As shown in FIG. 1 and FIG. 3, the clamp seat plate 204 is rectangular. The supporting rods 130 penetrate through four corners of the clamp seat plate 204 respectively. A position of one of the clamp seat plates 204 which is located at the fixed end 202 is unchanged relative to the four supporting rods 130, and another one of the clamp seat plates 204 which is located at the movable end 203 may drive the movable end 203 of the test piece clamp 200 to slide along extending directions of the supporting rods 130, so that tensile or compressive acting force is applied to the test piece 201 in the test piece clamp 200.

As long as a force acts on the movable end 203, an acting force may be generated on the test piece 201. As for which end serves as the fixed end and which end serves as the movable end and whether the creep test is a tensile creep test or a compressive creep test, it can be determined by limiting the movement of one end and allowing the other end to move relatively. According to a direction of the movement, the same device may be suitable for different creep tests.

The acting force is provided by the load loading mechanism 300. The load loading mechanism 300 includes a pulley block and a load 301. The pulley block includes at least one movable pulley 302 and multiple fixed pulleys. The load loading mechanism 300 is arranged above the test piece clamp 200. The fixed pulleys of the load loading mechanism 300 are fixed on the top plate 110. The load 301 is connected with the movable end 203 of the test piece clamp 201 through a steel wire rope 303 that is wound around the pulley block. The acting force is applied to the test piece 201 for a creep test by the load through the movable end 203 of the test piece clamp 200. The acting force acts on a same line as a central axis of the test piece 201. A direction of the acting force applied to the test piece clamp 200 is parallel to the extending directions of the supporting rods 130, so that the displacement of the movable end 203 can be realized.

Figure 2:
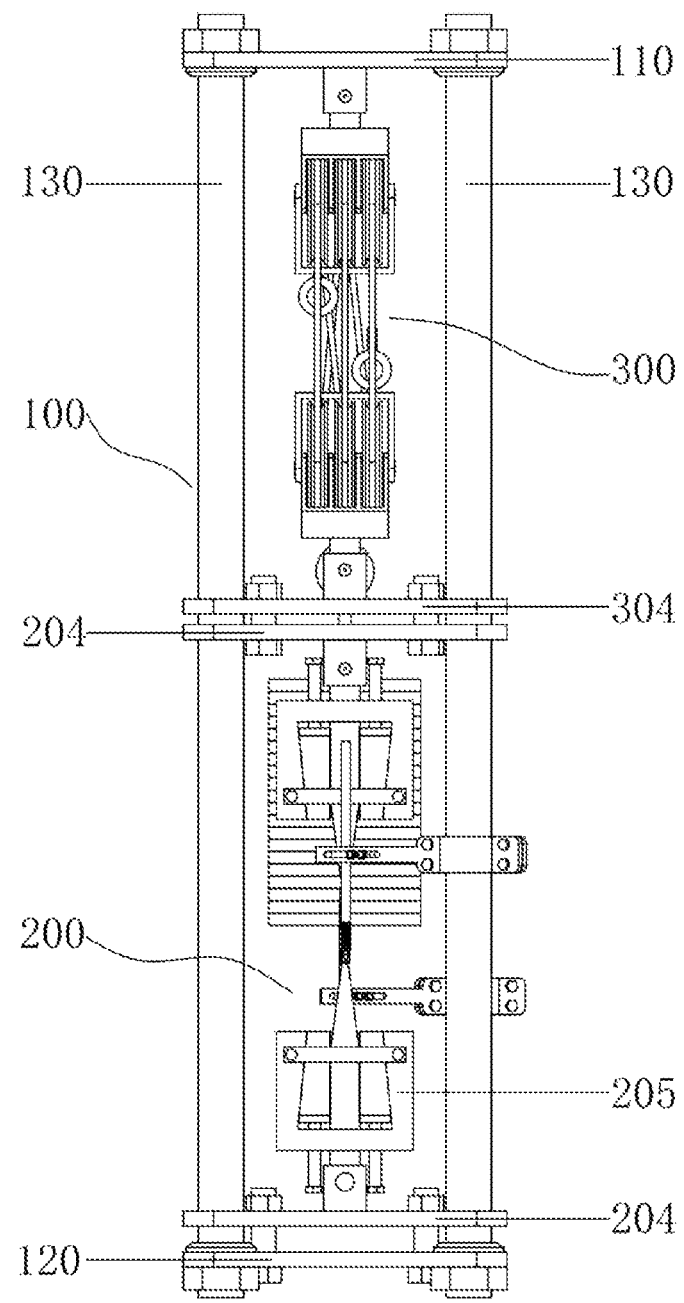
FIG. 2 is a side-view schematic diagram of the device for the tensile and creep test according to the present disclosure.

As shown in FIG. 1 and FIG. 2, when the tensile creep test is needed, the one of the clamp seat plates 204 on the test piece clamp 200 is close to the bottom plate 120, and may be fixedly connected with the bottom plate 120 to serve as the fixed end 202, and the another one of the clamp seat plates 204 is away from the bottom plate to serve as at the movable end 203, and is connected with the steel wire rope 303 of the load loading mechanism 300. Load 301 generates the acting force on the movable end 203 after the steel wire rope 303 is wound around the pulley block. Since the clamp seat plate 204 located at the movable end 203 is on the side which is close to the top plate 110 relative to the test piece, when the movable end 203 is pulled, the movable end 203 is pulled in a direction of the top plate 110, and a tensile acting force is generated on the test piece 201.

Figure 4:
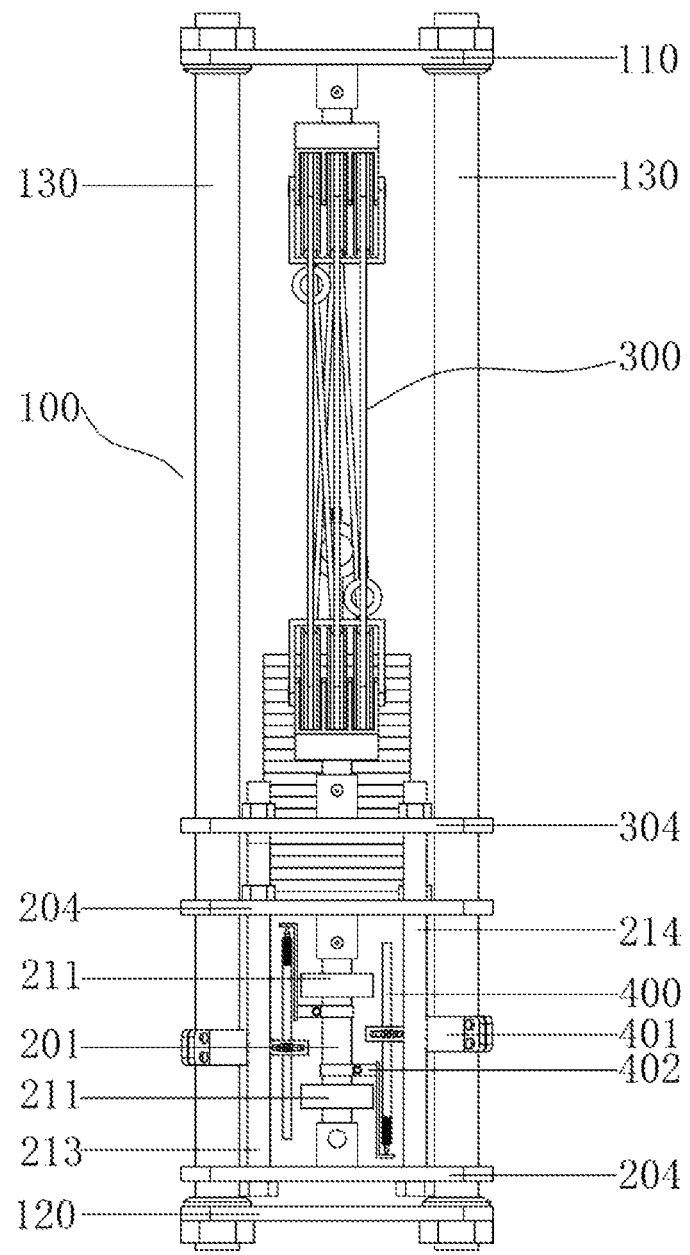
FIG. 4 is a side-view schematic diagram of the device for the compressive creep test according to the present disclosure.

As shown in FIG. 3 and FIG. 4, when the compressive creep test is needed, the one of the clamp seat plate 204 on the test piece clamp 200 is away from the bottom plate 120, and may be fixedly connected with the bottom plate 120 to serve as the fixed end 202, and the another one of the clamp seat plate 204 is close to the bottom plate to serve as the movable end 203, and is connected with the steel wire rope 303 of the load loading mechanism 300. The load 301 generates the acting force on the movable end 203 after the steel wire rope 303 is wound around the pulley block. Since the clamp seat plate 204 located at the movable end 203 is on the side which is close to the bottom plate 120 relative to the test piece, when the movable end 203 is pulled, the movable end 203 is pulled in the direction of the top plate 110, and the tensile acting force is generated on the test piece 201.

When a tensile test is carried out, the clamp seat plate 204 located at the fixed end 202 may be directly and fixedly connected with the bottom plate 120 through bolts, and the clamp seat plate 204 located at the movable end 203 may be directly connected with the steel wire rope 303, so that the test may be completed.

However, when a compressive test is carried out, the load loading mechanism 300 in the present embodiment cannot generate an acting force in the direction of the bottom plate 120. In order to compress the test piece, only the clamp seat plate 204 on the side, which is close to the top plate 110, may be fixed, and the compressive acting force is generated by pulling the clamp seat plate 204 which is close to the bottom plate 120. Fixation of the clamp seat plate 204 is not easy to achieve if the clamp seat plate 204 is directly and fixedly connected to the supporting rods, Because the whole device needs to ensure that a friction force between the supporting rod and the clamp seat plate is minimum in the experimental process, it is necessary to ensure that the surface of the supporting rod is smooth. Therefore, the surface of the supporting rod 130 cannot be destroyed by using a limiting structure or a locking structure because the clamp seat plate 204 needs to be fixed.

In addition, the load loading mechanism 300 is in transmission connection with the clamp seat plate 204 which is close to the bottom plate 120 after bypassing the clamp seat plate 204 which is closest to the load loading mechanism 300, and it is difficult to guarantee that the acting force may effectively and accurately act on the test piece 201.

Therefore, in the embodiment, a tail end of the wire rope 303 is provided with a load seat plate 304 which is parallel to the clamp seat plate 204, and the load seat plate 304 has substantially the same structure as the clamp seat plate 204. The four supporting rods 130 vertically penetrate through four corners of the load seat plate 304 similarly. The load seat plate 304 is in sliding fit with the supporting rods 130. The load seat plate 304 is fixedly connected with the clamp seat plate 204 which is at the movable end 203 of the test piece clamp 200 and drives the clamp seat plate 204 to move along the supporting rods 130. The acting force of the pulley block may be uniformly applied to the movable end 203 of the test piece clamp 200 through the load seat plate 304, so that the stability and the effectiveness of the acting force are guaranteed.

Figure 9:
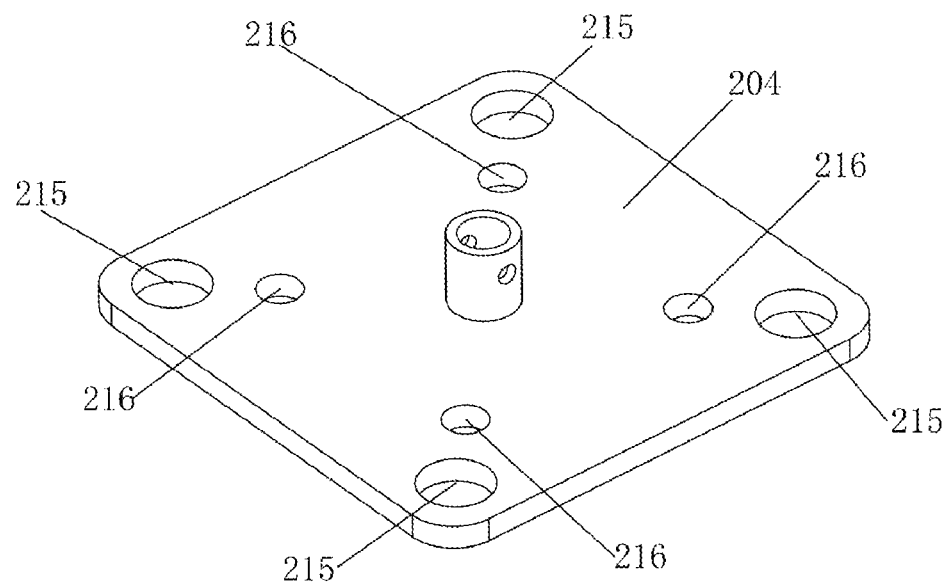
FIG. 9 is a structural schematic diagram of a clamp seat plate of the device for the creep test according to the present disclosure.

In the embodiment, a structure of the clamp seat plate 204 is as shown in FIG. 9. Through holes 215 through which the supporting rods 130 pass are provided in the positions near the four corners of the clamp seat plate 204. Four through holes 216 are also formed in diagonal lines of the corners and near the positions of the corners and are configured for bolts to pass through so as to connect the clamp seat plate 204 and the bottom plate 120. A structure of the load seat plate 304 is the same as that of the clamp seat plate 204, and the positions and sizes of the through holes of the load seat plate 304 are the same as that of the clamp seat plate 204.

As shown in FIG. 1, when the tensile test is carried out, the load seat plate 304 is fixedly connected with the clamp seat plate 204 which is closest to the load seat plate 304. As shown in FIG. 3 and FIG. 4, when the compressive test is carried out, the load seat plate 304 is fixedly connected with the clamp seat plate 204, which is close to the bottom plate 120, through two bolts 214 passing through two through holes 216 on the same diagonal line, and the clamp seat plate 204, which is close to the load seat plate 304, is fixedly connected with the bottom plate 120 through two bolts 213 passing through two through holes 216 on the other diagonal line. The bolts 214 and 213 need to pass through one clamp seat plate in addition to connecting two components, and the diameter of the through hole 216 should be larger than the diameters of the bolts 214 and 213 in order not to interfere with each other.

The movable pulley 302 in the embodiment is arranged above the load seat plate 304 and is rotatably connected with the load seat plate 304. That is, the load seat plate 304 is equivalent to a part of the movable pulley 302 to move along with the movable pulley 302.

As shown in FIG. 1 and FIG. 3, two fixed pulleys are provided, a first fixed pulley 305 is provided above the movable pulley 302, and a second fixed pulley 306 is provided on one side of the first fixed pulley 305. The first fixed pulley 305 and the second fixed pulley 306 are both rotatably connected with the top plate 110, and an axle of the first fixed pulley 305, an axle of the second fixed pulley 306 and an axle of the movable pulley 302 are parallel to each other. The first fixed pulley 305 and the movable pulley 302 are arranged up and down, which can guarantee that the acting force transmitted from the load 301 through the steel wire rope 303 may vertically act on the load seat plate 304.

The movable pulley 302 and the first fixed pulley 305 are each a three-wheel pulley set which includes three wheel pulleys, and the second fixed pulley 306 is a single wheel pulley. The steel wire rope 303 is wound between the movable pulley 302 and the first fixed pulley 305 and finally is wound the second fixed pulley 306. The steel wire rope 303 is wound between the movable pulley 302 and the first fixed pulley 305 in two ways, that is, a tail end of the steel wire rope 303 is either connected to a hook of the movable pulley 302 or a hook of the first fixed pulley 305, so that two acting force amplification ratios of the load 301 being 1:7 or 1:6 may be generated.

In this embodiment, the tail end of the steel wire rope 303 is first connected with the hook of the movable pulley 302, the steel wire rope 303 is wound between the movable pulley 302 and the first fixed pulley 305 for three circles, led out from the movable pulley 302 and then wound the second fixed pulley 306, and a front end of the steel wire rope 303 is connected vertically downwards to the load 301. Therefore, an acting force amplification effect of 1:7 may be generated.

The linear displacement sensors 400 are configured for acquiring displacement data of the test piece 201 during the creep test.

As shown in FIG. 1, FIG. 4, FIG. 5 and FIG. 7, two linear displacement sensors 400 are arranged. Each of the linear displacement sensors 400 is fixedly connected with the supporting rod 130, which is closest to a corresponding one of the linear displacement sensors 400, through respective sensor support 401. The variable quantities of the effective section of the test piece 201 needs to be tested no matter in the tensile creep test or the compressive creep test, so that the directions of probes of the linear displacement sensors 400 in each of the tensile creep test or the compressive creep test are opposite.

Two bearing platforms 402 are provided in a middle of the test piece 201 on the test piece clamp 200. One end of the bearing platform 402 is fixedly connected with the test piece 201, and the other end of the bearing platform 402 extends to a front of the probe of the linear displacement sensor 400. The bearing platforms 402 are fixed at two ends of the effective section of the test piece 201, and test values obtained by the linear displacement sensors 400 are the variable quantities of the effective section of the test piece 201.

Figure 5:
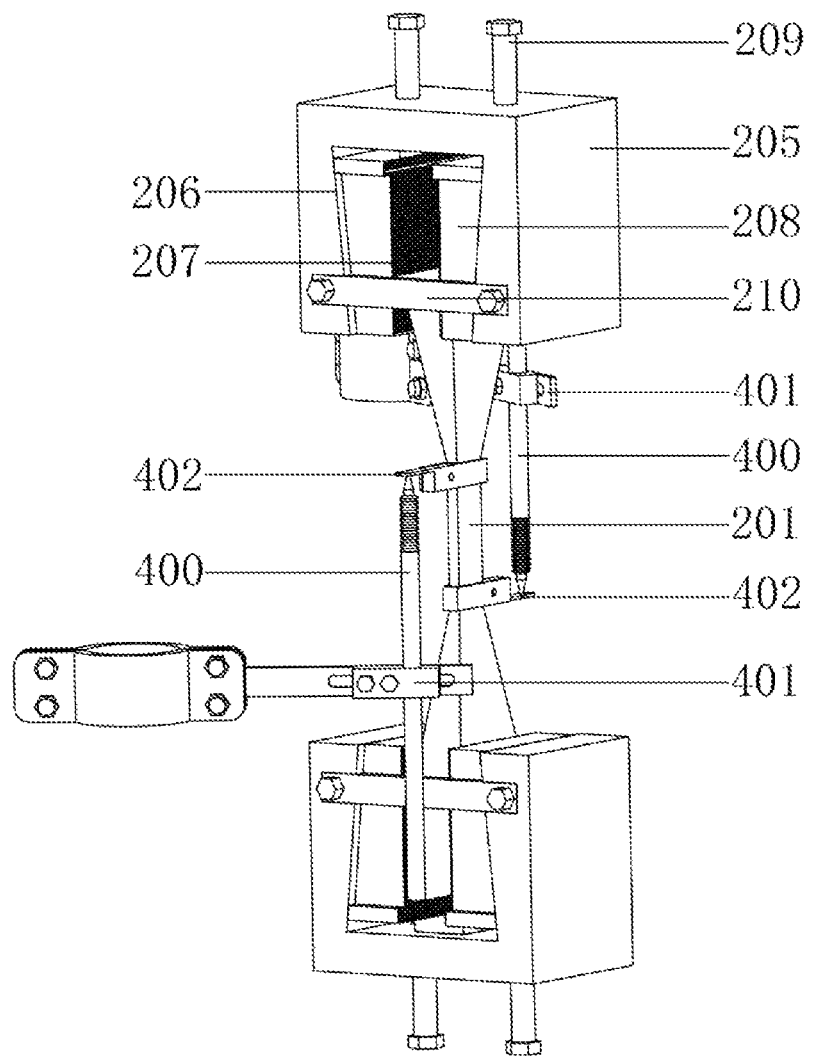
FIG. 5 is a schematic diagram of a test piece clamp of the device for the tensile creep test according to the present disclosure.
Figure 6:
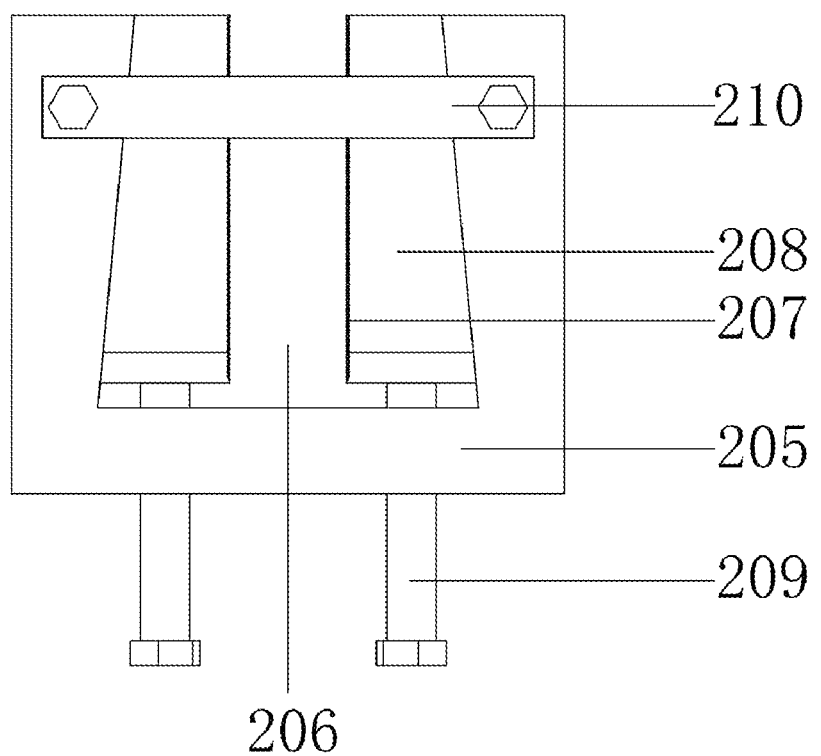
FIG. 6 is a schematic diagram of a tensile clamp seat of the device for the tensile and creep test according to the present disclosure.

According to a tensile device for a creep test in the present disclosure, as shown in FIG. 5, the test piece clamp 200 includes two tensile clamp seats 205. The tensile clamp seats 205 are respectively fixed on clamp seat plates 204. As shown in FIG. 6, an open groove 206 is formed in each tensile clamp seat 205. The open grooves 206 of two tensile clamp seats 205 are opposite to each other. Each of the open grooves 206 have two opposite sides and an opening between ends of the two sides. Two ends of test piece 201 are limited in the open grooves 206 of the tensile clamp seats 205 respectively.

Inner walls of two sides of the open groove 206 are provided with anti-slip patterns 207. The anti-skid lines 207 can effectively prevent the test piece 201 from displacing in the open groove 206 due to the acting force.

In order to better prevent the test piece 201 from moving along the direction of the acting force in the open groove 206 due to the acting force, the open groove 206 is a dovetail groove.

The inner walls of the open groove 206 are smooth. One wedge-shaped sliding block 208 is provided between the test piece 201 and one of the inner walls of the two sides of the open groove 206, and another wedge-shaped sliding block 208 is provided between the test piece 201 and another one of the inner walls of the two sides of the open groove 206. A shape of a side-view projection of each of the one wedge-shaped sliding block 208 and the another one wedge-shaped sliding block 208 is in a right trapezoid shape. A face, which is attached to the test piece 201, of each of the one wedge-shaped sliding block 208 and the another one wedge-shaped sliding block 208 is a vertical face. Anti-slip patterns 207 are provided on the vertical face. The vertical faces of the wedge-shaped sliding block 208 contact with the test piece 201 and clamp the test piece 201. The two ends of the test piece 201 do not need to be machined into the same cross section shape (trapezoid) as the open groove 206 and may be directly machined into a pair of parallel planes, so that the machining difficulty of the test piece 201 is reduced. The anti-skid patterns 207 on the vertical face can prevent the test piece 201 from displacing in the direction of the acting force relative to the wedge-shaped sliding block 208.

Puller bolts 209 are arranged at a bottom position, which is opposite to the opening of a corresponding one of the open grooves, of each of the two tensile clamp seats 205, and each of the puller bolts 209 and a corresponding one of the one wedge-shaped sliding block 208 and the another one wedge-shaped sliding block 208 are arranged in one-to-one correspondence. The puller bolt 209 penetrates through the bottom portion of a corresponding one of the tensile clamp seats 205 and abuts against an end, which is close to the bottom portion, of a respective one of the one wedge-shaped sliding block 208 and the another one wedge-shaped sliding block 208. Each of the puller bolt 209 is in screw-thread fit with the corresponding one of the tensile clamp seats 205. The wedge-shaped sliding block 208 is pushed towards a groove opening direction of the open groove 206 through the puller bolt 209, and transverse pressure on the two sides of each end of the test piece 201 may be generated, so that a better limiting effect of the test piece 201 is achieved.

A limiting rod 210 is arranged adjacent to the openings of the open groove 206. Two ends of the limiting rod 210 are fixedly connected with a corresponding one of the tensile clamp seats 205. The limiting rod 210 can not only strengthen clamping forces of the wedge-shaped sliding blocks 208 on the two sides of each end of the test piece 201, but also prevent the wedge-shaped sliding blocks 208 from sliding in the open grooves 206.

Figure 7:
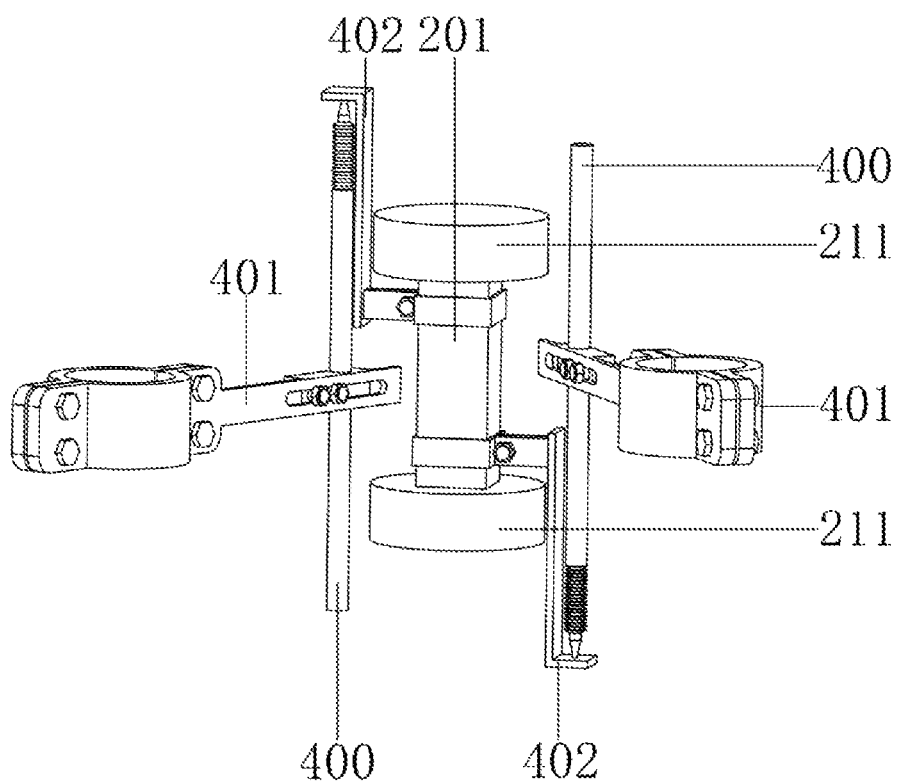
FIG. 7 is a schematic diagram of a test piece clamp of the device for the compressive and creep test according to the present disclosure.
Figure 8:
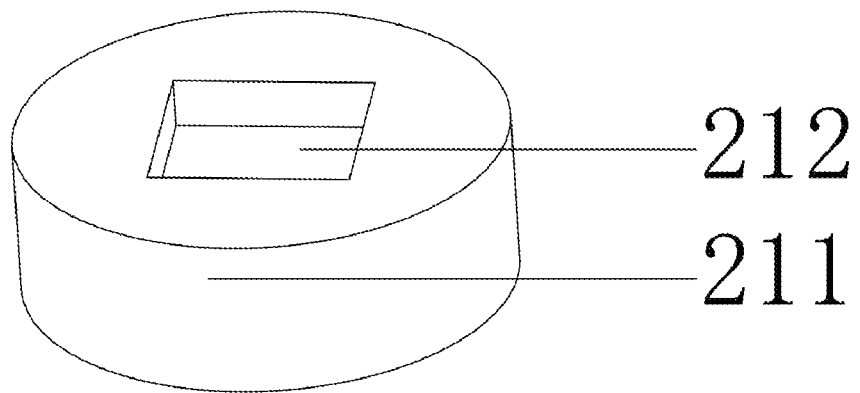
FIG. 8 is a schematic diagram of a pressure plate of the device for the compressive and creep test according to the present disclosure.

According to a compressive device for a creep test in the present disclosure, as shown in FIG. 7, the test piece clamp 200 includes two pressure plates 211. Each of the pressure plates 211 is fixed on a corresponding one of the clamp seat plates 204. As shown in FIG. 8, the two pressure plates 211 are provided with respective limiting grooves 212. The limiting grooves 212 of the two pressure plates 211 are opposite to each other. Each of the two ends of the test piece 201 is limited in a corresponding one of the limiting grooves 212 of the two pressure plates 211. The limiting groove 212 can prevent the test piece 201 from displacing in a non-acting force direction.

In the embodiment, each of fixed connection modes between the movable pulley 302 and the load seat plate 304, the two fixed pulleys and the top plate 110, and the test piece clamp and the clamp seat plate 204 is a connection mode that a connecting column 150, an annular connecting groove 151 and a pin 152 are respectively fixed on a bottom or a shell of each component. As shown in FIG. 14 to FIG. 17, the connecting columns 150 are provided on the first fixed pulley 305 and the second fixed pulley 306 respectively, and the annular connecting grooves 151 are formed in corresponding positions of the top plate 110. The connecting column 150 is provided on the movable pulley 302, and the annular connecting groove 151 is formed in a corresponding position of the load seat plate 304. The connecting column 150 is provided on the tensile clamp seat 205, and the annular connecting groove 151 is formed in a corresponding position of the clamp seat plate 204. The connecting column 150 is provided on the pressure plate 211, and the annular connecting groove 151 is formed in a corresponding position of the clamp seat plate 204. According to each group of components to be connected, after the connecting columns 150 on the components are inserted into the annular connecting grooves 151, the pins 152 are inserted into the pin holes reserved in the connecting columns 150 and the annular connecting grooves 151, and then connection is achieved.

According to the detachable connection mode, particularly for the test piece clamp 200, the tensile clamp seat 205 and the pressure plates 211 are convenient and fast to replace, and the test piece clamp may be arbitrarily selected and adjusted as required.

Figure 10:
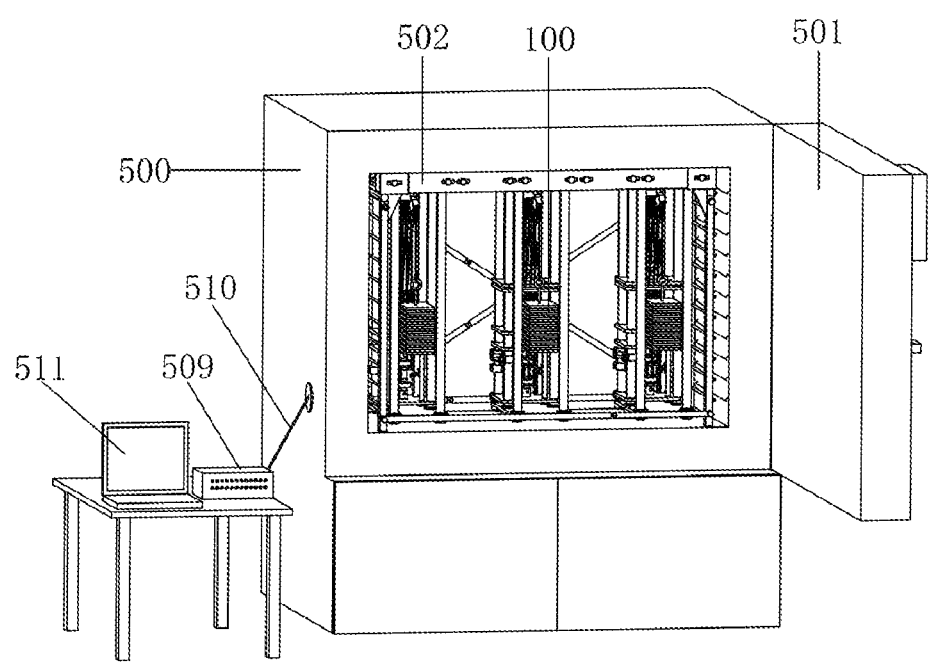
FIG. 10 is a structural schematic diagram of a system for a creep test according to the present disclosure.
Figure 11:
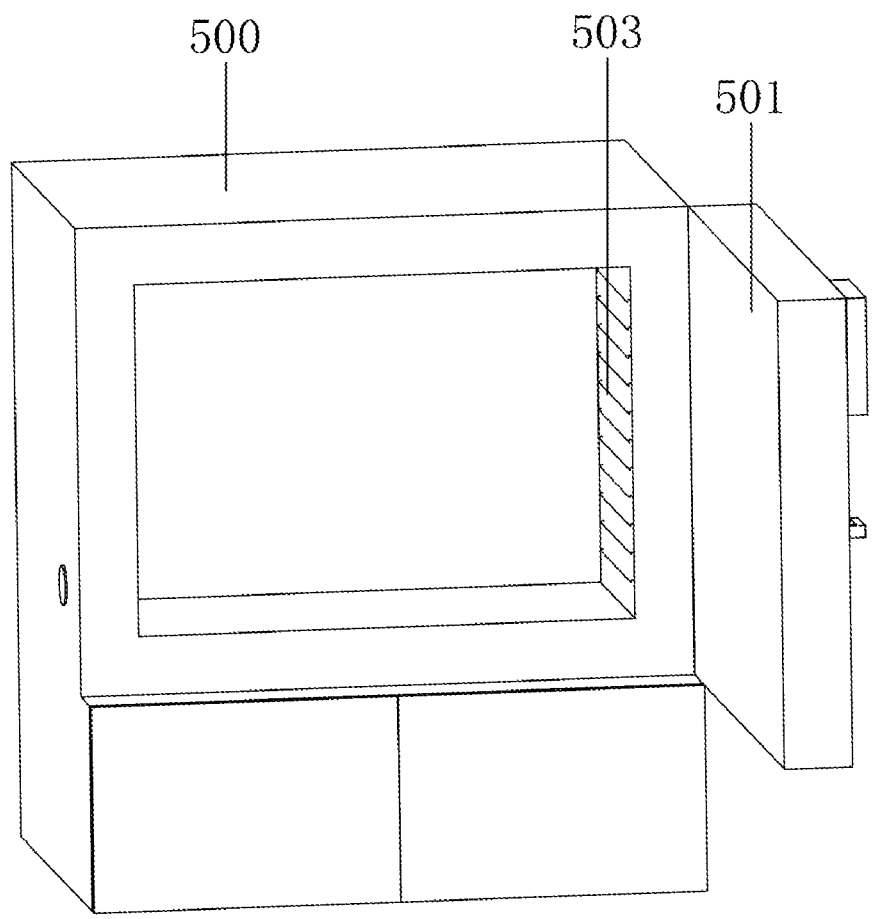
FIG. 11 is a structural schematic diagram of a box body of the system for the creep test according to the present disclosure.

A system for a tensile and compressive creep test provided by the present disclosure, as shown in FIG. 10, includes a box body 500 which is sealable. The box body 500 is provided with a box door 501. The box body 500 is provided with a constant temperature and humidity device. At least one device for the creep test is provided in the box body 500.

A rack 502 configured for fixing the device for the creep test is provided in the box body 500. At least one device for the creep test is provided on the rack 502. A top of the device frame 100 of the device for the creep test is horizontally fixed to a top of the rack 502. The length of the top plate and the length of the bottom plate of the device frame 100 are both equal to the width of the top of the rack 502.

Figure 12:
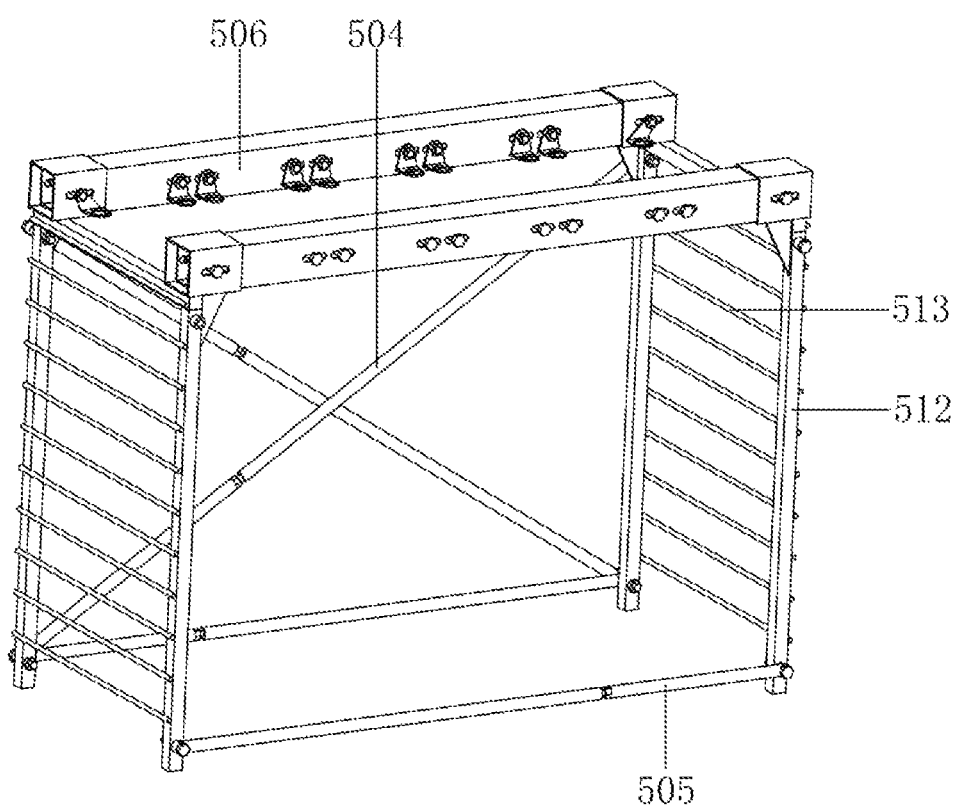
FIG. 12 is a structural schematic diagram of a rack of the system for the creep test according to the present disclosure.

As shown in FIG. 12, the rack 502 is of a rectangular frame structure and includes two top beams 506 located at a top of the rack 502, four side columns 512 and two bottom beams 505 located at a bottom of the rack 502. Multiple ribs 513 are sequentially arranged between the side columns 512 on two sides of the rack 502 at equal intervals from top to bottom. Multiple sliding strips 503 are arranged on inner walls of two sides of the box body 500 at equal intervals from top to bottom. The ribs 513 on the rack 502 are provided according to the sliding strips 503 in the box body 500. A distance between every adjacent two ribs 513 is equal to a distance between every adjacent two sliding strips 503.

When the rack 502 is pushed into the box body 500, the ribs 513 correspond to the sliding strips 503 and then are pushed into the box body 500. The sliding strips 503 serve as sliding rails of the ribs 513 and also serve as bearing of the whole rack 502.

In practical application, the bottom of the rack 502 is not in contact with the bottom plate in the box body 500. The device for the creep test is suspended in the box body 500, because the bottom plate in the box body 500 is thin and cannot bear large-mass load. Moreover, the device for the creep test is suspended, so that climate parameters in the box body 500 are more uniform.

Because the top beams 506 of the rack 502 are required to bear the weight of the whole device for the creep test, the top beams 506 may be made of concentric-square-shaped steel with the larger diameter, which has a higher bearing capacity. Since the rack 502 is of a rectangular structure and creep tests require the rack 502 to be kept naturally vertical, in addition to ensuring that the top beams 506 do not deform and the whole rack 502 cannot deform. In order to adjust the rack 502, the bottom beams 505 are two rods of variable length, each bottom beam 505 includes two sections of rods in threaded connection, so that the length of the bottom beam 505 may be adjusted.

Preferably, two connecting beams 504 are arranged diagonally on an inner side of the rack 502. The connecting beam 504 also includes two sections of rods in threaded connection, so that the levelness of the rack 502 may be adjusted by adjusting the lengths of the connecting beams 504.

All components of the rack 502 are connected through bolts. Screw holes are strip-shaped holes, so that fixed positions of the bolts may be adjusted.

Figure 13:
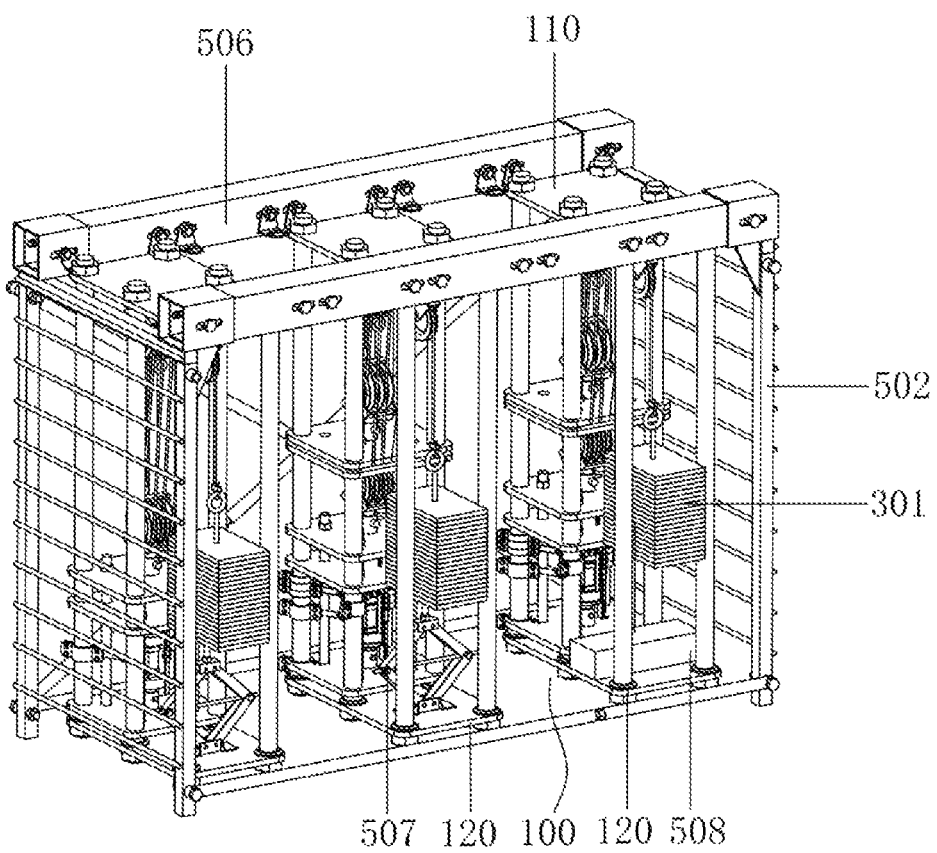
FIG. 13 is a using state diagram of a rack of the system for the creep test according to the present disclosure.
Figure 14:
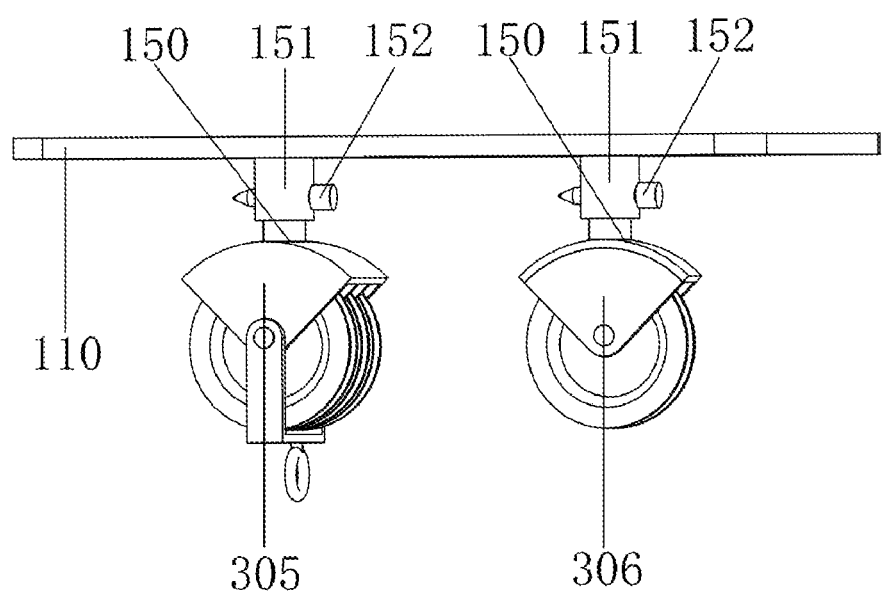
FIG. 14 is a schematic diagram of a connecting structure of a first fixed pulley, a second fixed pulley and a top plate.
Figure 15:
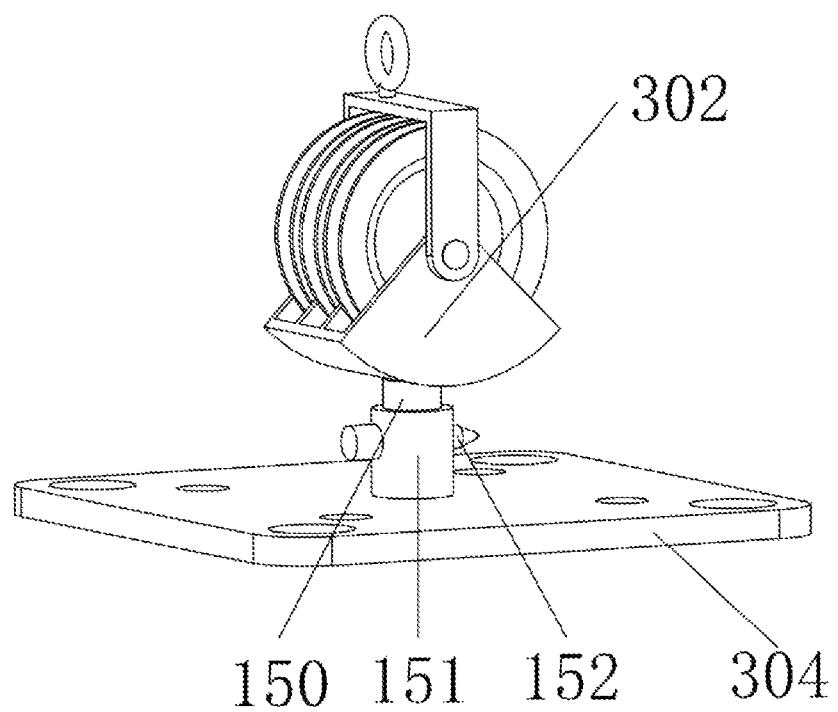
FIG. 15 is a schematic diagram of a connecting structure of a movable pulley and a load seat plate.
Figure 16:
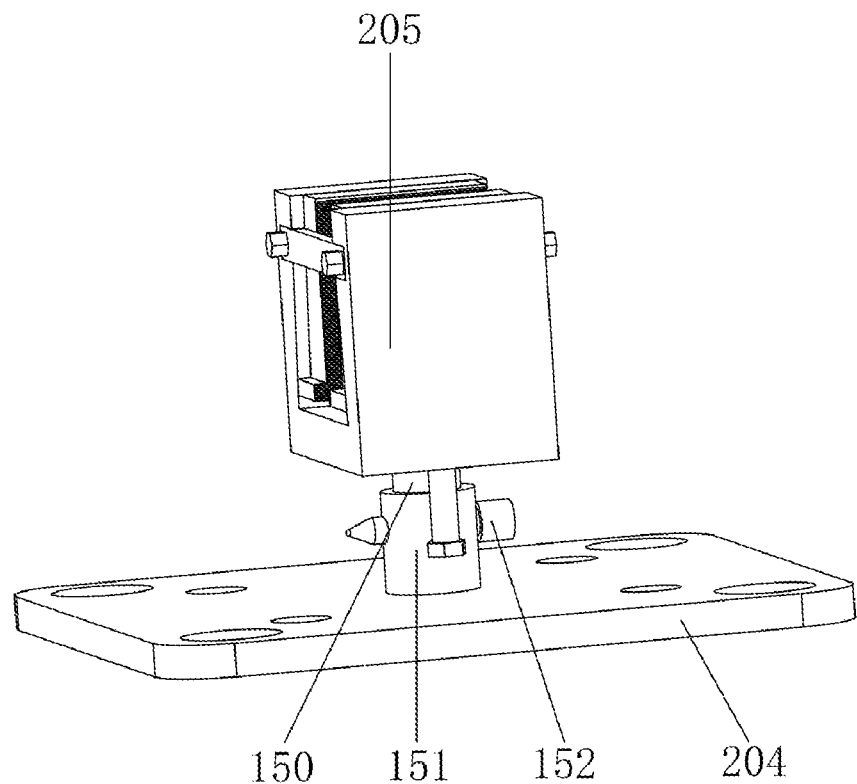
FIG. 16 is a schematic diagram of a connecting structure of a tensile clamp seat and a clamp seat plate.
Figure 17:
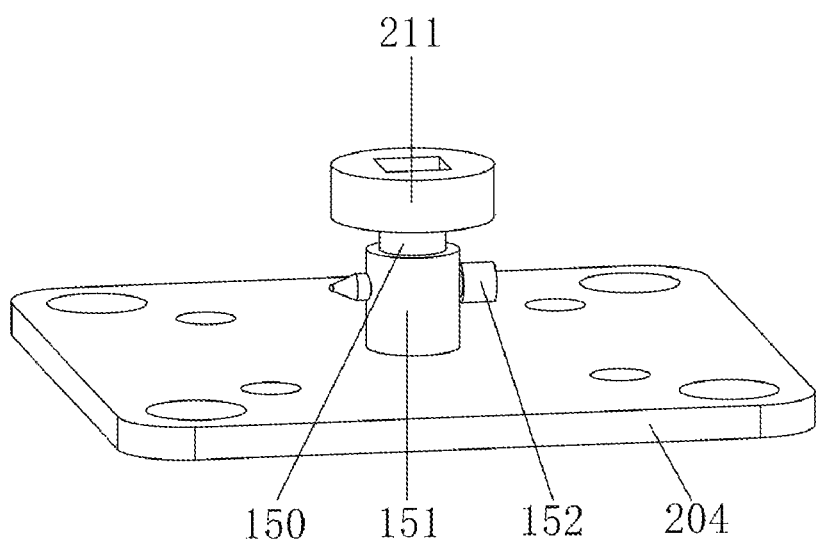
FIG. 17 is a schematic diagram of a connecting structure of a pressure plate and the clamp seat plate.

As shown in FIG. 13, in the embodiment, two devices for the creep test are provided in the box body 500, so that both tensile and compressive creep tests may be carried out simultaneously for the same material.

As shown in FIG. 1 to FIG. 4, the length of the clamp seat plate 204 is equal to the length of the load seat plate 304, and the length of each of the clamp seat plates 204 and the length of the load seat plate 304 are smaller than the length of the bottom plate 110. The supporting rods 130 includes six supporting rods. Two of the six supporting rods 130 which are close to the box door 501 are connected with the top plate 110 and the bottom plate 120, and the other four of the six supporting rods 130 are connected with the top plate 110 and the bottom plate 120 and penetrate through the clamp seat plates 204 and the load seat plate 304.

The load 301 of the load loading mechanism is arranged close to the box door 501, so that the acting force is convenient to control through the load.

The first fixed pulley 305 and the second fixed pulley 306 of the load loading mechanism 300 are arranged side by side along a center line of the top plate 110 in a length direction of the top plate, and the movable pulley 302 is located directly under the first fixed pulley 305. A central axes and a gravity center of the first fixed pulley 305, a central axis and a gravity center of the movable pulley 302, a central axis and a gravity center of the load seat plate 304, a central axis and a gravity center of the clamp seat plates 204, a central axis and a gravity center of the test piece clamp 200 and a central axis and a gravity center of the test piece 201 are on the same vertical line, which can guarantee that the acting force may be effectively transmitted to the test piece.

As shown in FIG. 13, a lifting device 507 is arranged directly under the load 301 and placed on the bottom plate 120. The lifting device 507 in the embodiment is a jack, and a scissor jack may be selected. The use of the scissor jack can avoid damage to the linear displacement sensors 400 and the rack 502 due to the shock loading of the whole system caused by sudden loading.

A buffer cushion 508 is laid on the bottom plate 120 that is directly under the load 301. The buffer cushion 508 is mainly configured for preventing equipment damage caused by falling of the load 301 when the test piece is pulled and broken by the load 301 in the test process.

The box body 500, namely an environmental climate box, in the embodiment is selected from a BINDER KMF720 environmental climate box in Germany. The linear displacement sensor is selected from an F50-10LVDT displacement sensor of Shenzhen Woke Intelligent System Ltd. Co. The box body 500 is further internally provided with an air inlet system, an air speed adjusting device, a temperature and humidity sensor. A temperature and humidity alarm device, a computer and a power supply for the test system are provided outside the box body 500. The air speed adjusting device includes a hot wire type anemometer and a rotating speed adjuster. The air speed adjusting device and the temperature and humidity sensor not only have the capacity of stably generating, conveying, maintaining and discharging wet air with specific humidity and temperature in a quantitative, constant-speed and directional manner, so as to ensure that the wood test piece can stably absorb or discharge gaseous moisture, bue also have the capacity of adjusting and controlling the humidity, the temperature, the flow velocity and the change amplitude of the wet air, so as to ensure that the relative humidity control precision of the wet air is not greater than +/−2%, and the temperature control precision is not greater than +/−0.1° C. During practical implementation, in order to prevent the influence of daily changes of the humidity and temperature of the surrounding environment of the box body (especially the influence of door opening) on the humidity and temperature in the box body, and maintain the consistency of the temperature and humidity of the experimental operation space outside the box body and the parameters in the box body as much as possible, the test may be carried out in an environment provided with a humidifier/dehumidifier and an air conditioner. The adjustable range of the ambient temperature around the box body is 10-40° C., and the precision of the ambient temperature around the box body is +/−1° C. The adjustable range of the relative humidity of the wet air is 40-80%, and the precision of the relative humidity of the wet air is +/−5%.

A test method using a system for a tensile and compressive creep test in the present disclosure includes, for each of at least one device for the creep test comprised in the system for the tensile and compressive creep test, the following steps one to six.

In step one, a test piece clamp is selected according to a test purpose, a test piece to be tested is installed in the test piece clamp, one clamp seat plate that is provided at a fixed end of the test piece clamp is fixed, and another one clamp seat plate that is provided at a movable end of the test piece clamp is fixedly connected with a load seat plate.

In step two, bearing platforms is installed on the test piece, positions of linear displacement sensors are fixed, and a probe of each of the linear displacement sensors is abutted against a surface of a corresponding one of the bearing platforms.

In step three, a lifting device is placed on a bottom plate, and the load is lifted by the lifting device and is connected with the steel wire rope.

In step four, the lifting device is lowered until the load is suspended, the lifting device is taken out, and a buffer cushion is laid on the bottom plate that is directly under the load.

In step five, a box door is closed, a constant temperature and humidity device is started to control temperature and humidity in the box body, and data is monitored in real time.

In step six, the temperature, the humidity and an air speed in the box body and the displacement signals of the test piece acquired in the fifth step are inputted into a computer for data storage, processing analysis and display.

As shown in FIG. 10, the acquired temperature, humidity and displacement signals are input into the computer 511 through a transmitter 509 and a data wire 510. Real-time storage, real-time processing analysis and display of data can be achieved through program software compiled based on a VB language. The acquired real-time original data are stored in a database form in a text format and are configured for software real-time data processing and analysis. The data may be exported at any time to be copied into a backup, which facilitates offline processing and analysis of the data. The data are obtained by the temperature and humidity sensor. After the data are recorded and processed by matched software, a real-time coordinate graph with time as a horizontal mark and temperature and relative humidity in the box body as longitudinal marks may be obtained. After real-time processing is carried out on the original displacement data by software, a continuous coordinate graph by taking time as a horizontal mark and static bending deflection and wet expansion and dry shrinkage of the test piece as vertical marks is formed for real-time monitoring and monitoring.

What is claimed is:

1. A device for a creep test, the device comprising a device frame, a test piece clamp, a load loading mechanism and linear displacement sensors, wherein each of the test piece clamp, the load loading mechanism and the linear displacement sensors is arranged on the device frame, wherein:
    the test piece clamp is configured for placing a test piece for the creep test, the test piece is arranged in a middle of the test piece clamp, a first end of the test piece clamp is a fixed end, a position of the fixed end is unchanged relative to the device frame, and a second end of the test piece clamp is a movable end;
    the load loading mechanism comprises a pulley block and a load, the pulley block comprises at least one movable pulley and a plurality of fixed pulleys, the load is connected with the movable end of the test piece clamp through a steel wire rope that is wound around the pulley block, an acting force is applied to the test piece for the creep test by the load through the movable end of the test piece clamp, and the acting force acts on a same line as a central axis of the test piece; and
    the linear displacement sensors are configured for acquiring displacement data of the test piece during the creep test.

2. The device for the creep test according to claim 1, wherein the device frame comprises a top plate and a bottom plate which are arranged up and down opposite to each other, and the top plate and the bottom plate are fixedly connected through at least four supporting rods which are arranged parallel to each other.

3. The device for the creep test according to claim 2, wherein a direction of the acting force applied to the test piece clamp is parallel to extending directions of the at least four supporting rods, the load loading mechanism is arranged above the test piece clamp, and the plurality of fixed pulleys of the load loading mechanism are fixed on the top plate.

4. The device for the creep test according to claim 3, wherein the fixed end and the movable end of the test piece clamp are fixedly provided with respective clamp seat plates; four supporting rods of the at least four supporting rods vertically penetrate through the clamp seat plates, a position of one of the clamp seat plates which is located at the fixed end is unchanged relative to the four supporting rods, and another one of the clamp seat plates which is located at the movable end is slideable along the extending directions of the four supporting rods.

5. The device for the creep test according to claim 4, wherein the one of the clamp seat plates on the test piece clamp is close to the bottom plate and is fixedly connected with the bottom plate to serve as the fixed end; and the another one of the clamp seat plates is away from the bottom plate to serves as the movable end, and is connected with the steel wire rope of the load loading mechanism.

6. The device for the creep test according to claim 4, wherein the one of the clamp seat plates on the test piece clamp is away from the bottom plate and is fixedly connected with the bottom plate to serve as the fixed end; and the another one of the clamp seat plates is close to the bottom plate to serve as the movable end, and is connected with the steel wire rope of the load loading mechanism.

7. The device for the creep test according to claim 5, wherein a load seat plate parallel to the clamp seat plates is arranged at a tail end of the steel wire rope, the four supporting rods vertically penetrate through the load seat plate which is in sliding fit with the four supporting rods, the load seat plate is fixedly connected with the another one of the clamp seat plates which is at the movable end of the test piece clamp, the at least one movable pulley is arranged above the load seat plate and rotatably connected with the load seat plate, the plurality of fixed pulleys comprise two fixed pulleys, a first fixed pulley of the two fixed pulleys is arranged above the at least one movable pulley, a second fixed pulley of the two fixed pulleys is arranged on one side of the first fixed pulley, the first fixed pulley and the second fixed pulley are rotatably connected with the top plate, an axle of the first fixed pulley, an axle of the second fixed pulley and an axle of the movable pulley are parallel to each other, the at least one movable pulley and the first fixed pulley are each a three wheel pulley set, the second fixed pulley is a single wheel pulley, the tail end of the steel wire rope is connected with a hook of the at least one movable pulley, the steel wire rope is wound between the movable pulley and the first fixed pulley for three circles, led out from the movable pulley and wound around the second fixed pulley, and a front end of the steel wire rope is connected vertically downwards to the load.

8. The device for the creep test according to claim 6, wherein a load seat plate parallel to the clamp seat plates is arranged at a tail end of the steel wire rope, the four supporting rods vertically penetrate through the load seat plate which is in sliding fit with the four supporting rods, the load seat plate is fixedly connected with the another one of the clamp seat plates which is at the movable end of the test piece clamp, the at least one movable pulley is arranged above the load seat plate and rotatably connected with the load seat plate, the plurality of fixed pulleys comprise two fixed pulleys, a first fixed pulley of the two fixed pulleys is arranged above the at least one movable pulley, a second fixed pulley of the two fixed pulleys is arranged on one side of the first fixed pulley, the first fixed pulley and the second fixed pulley are rotatably connected with the top plate, an axle of the first fixed pulley, an axle of the second fixed pulley and an axle of the movable pulley are parallel to each other, the movable pulley and the first fixed pulley are each a three wheel pulley set, the second fixed pulley is a single wheel pulley, the tail end of the steel wire rope is connected with a hook of the movable pulley, the steel wire rope is wound between the movable pulley and the first fixed pulley for three circles, led out from the movable pulley and wound around the second fixed pulley, and a front end of the steel wire rope is connected vertically downwards to the load.

9. The device for the creep test according to claim 3, wherein the linear displacement sensors comprises two linear displacement sensors, each of the two linear displacement sensors is fixedly connected with a nearest supporting rod of the at least four supporting rods through respective sensor support, and directions of probes of the two linear displacement sensors are opposite; and two bearing platforms are arranged in a middle of the test piece in the test piece clamp, for each of the two bearing platforms,
a first end of the bearing platform is fixedly connected with the test piece, and a second end of the bearing platform extends to a front of a corresponding one of the probes of the two linear displacement sensors.

10. The device for the creep test according to claim 5, wherein the test piece clamp comprises two tensile clamp seats, each of the two tensile clamp seats is fixed on a corresponding one of the clamp seat plates, open grooves are respectively formed in the two tensile clamp seats, wherein each of the open grooves has two opposite sides and an opening between ends of the two sides, the open grooves of the two tensile clamp seats are opposite to each other, two ends of the test piece are respectively limited in the open grooves of the two tensile clamp seats, inner walls of the two sides of each of the open grooves are provided with anti-slip patterns, and each of the open grooves is a dovetail groove.

11. The device for the creep test according to claim 10, wherein for each of the open grooves,
the inner walls of the open groove are smooth, one wedge-shaped sliding block is arranged between the test piece and one of the inner walls of the two sides of the open groove, and another one wedge-shaped sliding block is arranged between the test piece and another one of the inner walls of the two sides of the open groove;
a shape of a side-view projection of each of the one wedge-shaped sliding block and the another one wedge-shaped sliding block is a right trapezoid shape, a face, which is attached to the test piece, of each of the one wedge-shaped sliding block and the another one wedge-shaped sliding block is a vertical face, and anti-slip patterns are arranged on the vertical face.

12. The device for the creep test according to claim 11, wherein puller bolts are arranged on a bottom portion, which is opposite to the opening of a corresponding one of the open grooves, of each of the two tensile clamp seats, and each of the puller bolts and a corresponding one of the one wedge-shaped sliding block and the another one wedge-shaped sliding block are arranged in one-to-one correspondence; each of the puller bolts penetrates through the bottom portion of a corresponding one of the two tensile clamp seats and abuts against an end, which is close to the bottom portion, of a respective one of the one wedge-shaped sliding block and the another one wedge-shaped sliding block, and each of the puller bolts is in screw-thread fit with the corresponding one of the two tensile clamp seats.

13. The device for the creep test according to claim 11, wherein a limiting rod is arranged adjacent to the opening of each of the open grooves, and two ends of the limiting rod are fixedly connected with a corresponding one of the two tensile clamp seats.

14. The device for the creep test according to claim 6, wherein the test piece clamp comprises two pressure plates, each of the two pressure plates is fixed on a corresponding one of the clamp seat plates, the two pressure plates are provided with respective limiting grooves, the limiting grooves of the two pressure plates are opposite to each other, and each of the two ends of the test piece is limited in a corresponding one of the limiting grooves of the two pressure plates.

15. A system for a tensile and compressive creep test, the system comprising a box body which is sealable, wherein the box body is provided with a box door, the box body is provided with a constant temperature and humidity device, and wherein at least one device for the creep test is arranged in the box body, wherein each of the at least one device for the creep test comprises a device frame, a test piece clamp, a load loading mechanism and linear displacement sensors, wherein each of the test piece clamp, the load loading mechanism and the linear displacement sensors is arranged on the device frame, wherein:

the test piece clamp is configured for placing a test piece for the creep test, the test piece is arranged in a middle of the test piece clamp, a first end of the test piece clamp is a fixed end, a position of the fixed end is unchanged relative to the device frame, and a second end of the test piece clamp is a movable end;
the load loading mechanism comprises a pulley block and a load, the pulley block comprises at least one movable pulley and a plurality of fixed pulleys, the load is connected with the movable end of the test piece clamp through a steel wire rope that is wound around the pulley block, an acting force is applied to the test piece for the creep test by the load through the movable end of the test piece clamp, and the acting force acts on a same line as a central axis of the test piece; and
the linear displacement sensors are configured for acquiring displacement data of the test piece during the creep test.

16. The system for tensile and compressive creep test according to claim 15, wherein a rack configured for fixing the at least one device for the creep test is arranged in the box body, the at least one device for the creep test is arranged on the rack, a top of the device frame of each of the at least one device for the creep test is horizontally fixed to a top of the rack, the device frame comprises a top plate and a bottom plate which are arranged up and down opposite to each other, and the top plate and the bottom plate are fixedly connected through at least four supporting rods that are arranged parallel to each other, and a length of the top plate and a length of the bottom plate of the device frame are equal to a width of the top of the rack.

17. The system for the tensile and compressive creep test according to claim 16, wherein for each of the at least one device for the creep test,
the fixed end and the movable end of the test piece clamp are fixedly provided with respective clamp seat plates, a load seat plate parallel to the clamp seat plates is arranged at a tail end of the steel wire rope, a length of each of the clamp seat plates is equal to a length of the load seat plate, and the length of each of the clamp seat plates and the length of the load seat plate are smaller than the length of the bottom plate;

the supporting rods comprises six supporting rods, two of the six supporting rods which are close to the box door are connected with the top plate and the bottom plate, and other four of the six supporting rods are connected with the top plate and the bottom plate and penetrate through the clamp seat plates and the load seat plate.

18. The system for the tensile and compressive creep test according to claim 17, wherein the load of the load loading mechanism of each of the at least one device for the creep test is arranged close to the box door.

19. The system for the tensile and compressive creep test according to claim 18, wherein for each of the at least one device for the creep test, the at least one movable pulley is arranged above the load seat plate and rotatably connected with the load seat plate, the plurality of fixed pulleys comprise two fixed pulleys, a first fixed pulley of the two fixed pulleys is arranged above the at least one movable pulley, a second fixed pulley of the two fixed pulleys is arranged on one side of the first fixed pulley, the first fixed pulley and the second fixed pulley are rotatably connected with the top plate, an axle of the first fixed pulley, an axle of the second fixed pulley and an axle of the movable pulley are parallel to each other, the at least one movable pulley and the first fixed pulley are each a three wheel pulley set, the second fixed pulley is a single wheel pulley, the tail end of the steel wire rope is connected with a hook of the at least one movable pulley, the steel wire rope is wound between the movable pulley and the first fixed pulley for three circles, led out from the movable pulley and wound around the second fixed pulley, and a front end of the steel wire rope is connected vertically downwards to the load; the first fixed pulley and the second fixed pulley of the load loading mechanism are arranged side by side along a center line of the top plate in a length direction of the top plate, and the at least one movable pulley is located directly under the first fixed pulley; and a central axis and a gravity center of the first fixed pulley, a central axis and a gravity center of the at least one movable pulley, a central axis and a gravity center of the load seat plate, a central axis and a gravity center of each of the clamp seat plates, a central axis and a gravity center of the test piece clamp and a central axis and a gravity center of the test piece are on a same vertical line, a lifting device is arranged directly under the load and placed on the bottom plate, the lifting device is a jack, and a buffer cushion is laid on the bottom plate that is directly under the load.

\* \* \* \* \*